United States Patent
Loumaye et al.

(10) Patent No.: US 9,168,264 B2
(45) Date of Patent: Oct. 27, 2015

(54) TREATMENT OF EXCESSIVE MENSTRUAL BLEEDING ASSOCIATED WITH UTERINE FIBROIDS

(75) Inventors: Ernest Loumaye, Cologny (CH); Elke Bestel, Sant-Julien-en-Genevois (FR); Ian Osterloh, Kent (GB)

(73) Assignee: PREGLEM SA, Geneva (CH)

( * ) Notice: Subject to any disclaimer, the term of this patent is extended or adjusted under 35 U.S.C. 154(b) by 0 days.

(21) Appl. No.: 14/131,857

(22) PCT Filed: Jul. 12, 2012

(86) PCT No.: PCT/IB2012/053577
§ 371 (c)(1),
(2), (4) Date: Jan. 9, 2014

(87) PCT Pub. No.: WO2013/008202
PCT Pub. Date: Jan. 17, 2013

(65) Prior Publication Data
US 2014/0148419 A1 May 29, 2014

(30) Foreign Application Priority Data
Jul. 12, 2011 (EP) .................................... 11173630

(51) Int. Cl.
*A61K 31/58* (2006.01)
*A61K 31/573* (2006.01)
*A61K 31/57* (2006.01)

(52) U.S. Cl.
CPC .............. *A61K 31/573* (2013.01); *A61K 31/57* (2013.01)

(58) Field of Classification Search
USPC ................................................. 514/172, 179
See application file for complete search history.

(56) References Cited

U.S. PATENT DOCUMENTS

| | | | |
|---|---|---|---|
| 4,954,490 A | 9/1990 | Cook et al. | |
| 5,073,548 A | 12/1991 | Cook et al. | |
| 5,929,262 A | 7/1999 | Kim et al. | |
| 6,451,780 B1 * | 9/2002 | Chwalsz et al. | 514/179 |
| 6,900,193 B1 * | 5/2005 | Kim et al. | 514/179 |
| 8,569,274 B2 * | 10/2013 | Fauser et al. | 514/172 |
| 2006/0247234 A1 * | 11/2006 | Nagi et al. | 514/230.5 |
| 2007/0213306 A1 | 9/2007 | Hausknecht | |
| 2009/0118253 A1 | 5/2009 | As et al. | |
| 2009/0192130 A1 * | 7/2009 | Nieman et al. | 514/178 |
| 2014/0005157 A1 * | 1/2014 | Rubin | 514/179 |

FOREIGN PATENT DOCUMENTS

| WO | WO 2004/065405 A1 | 8/2004 |
|---|---|---|
| WO | WO 2004/078709 A2 | 9/2004 |
| WO | WO 2007/103510 A2 | 9/2007 |
| WO | WO2008129396 * | 10/2008 |

OTHER PUBLICATIONS

Xu et al. CAS: 154: 302159, 2010.*
Cole et al. CAS: 145: 240652, 2006.*
Ambat, S., et al, "Uterine Artery Embolization Versus Laparoscopic Occlusion of Uterine Vessels For Management of Symptomatic Uterine Fibroids," *International Journal of Gynecology and Obstertrics* 105(2): 162-165, Elsevier Ireland Ltd., Ireland (2009).
American Society for Reproductive Medicine "Myomas and Reproductive Function" *Fertility and Sterility 90*: 125-130, Elsevier Inc., United States (2008).
Attardi, B.J., et al., "In Vitro Antiprogestational/Antiglucocorticoid Activity and Progestin and Glucocorticoid Receptor Binding of the Putative Metabolites and Synthetic Derivatives of CDB-2914, CDB-4124, and Mifepristone," *The Journal of Steroid Biochemistry & Molecular Biology 88*: 277-288, Elsevier Ltd., England (2004).
Blithe, D.L. et al., "Development of the Selective Progesterone Receptor Modulator CDB-2914 for Clinical Indications," *Steroids 68*: 1013-1017, Elsevier Inc., United States (2003).
Busfield, R.A., et al., "A Randomised Trial Comparing the Levonorgestrel Intrauterine System and Thermal Balloon Ablation for Heavy Menstrual Bleeding," *BJOG An International Journal of Obstetrics and Gynacology 113*: 257-263, Blackwell Publishing, England (2006).
Chwalisz, K. et al., "Selective Progesterone Receptor Modulator Development and Use in the Treatment of Leiomyomata and Endometriosis," *Endocrine Revies 26*(3): 423-438, The Endocrine Society, The United States (2005).
The ESHRE Capri Workshop Group, "Endometrial Bleeding" *Human Reproduction Update 13*(5): 421-431, Oxford University Press, England (2007).
Donnez, J. and Jadoul, P., "What are the Implications of Myomas on Fertility? A Need For Debate?" *Human Reproduction Update 17*(6): 1424-1430, European Society of Human Reproduction And Embryology, Belgium (2002).
Goodwin, S.C., et al., "Uterine Artery Embolization for the Treatment of Uterine Leiomyomata: Midterm Results," *Journal of Vascular and Interventional Radiology 10*(9): 1159-1165, Society of Interventional Radiology, United States (1999).
Grow, D.R. and Filer, R.B., "Treatment of Adenomyosis with Long-Tem Gnrh Analogues: A Case Report," *Obsterics & Gynecology 78*: 538-539, Elsevier Inc., United States (1991).
Higham, J. M., "Assessment of Menstrual Blood Loss Using a Pictorial Chart, "*British Journal of Obstetrics and Gynaecology 97*: 734-739, Blackwell Scientific Publishing, United Kingdom (1990).
Janssen, C.A., "A Simple Visual Assessment Technique to Discriminate Between Menorrhagia and Normal Menstrual Blood Loss," *European Journal of Obstetrics & Gynecology 70*: 21-22, Elsevier Science Ireland Ltd., Ireland (1996).

(Continued)

*Primary Examiner* — Rei-Tsang Shiao
(74) *Attorney, Agent, or Firm* — Sterne, Kessler, Goldstein & Fox P.L.L.C.

(57) ABSTRACT

The present invention relates generally to benign gynecological diseases and in particular to a method and compositions for reducing heavy menstruation associated with said gynecological diseases following treatment with vascular occlusion methods or thermal related treatment methods.

20 Claims, No Drawings

(56) References Cited

OTHER PUBLICATIONS

Kadir, R.A., et al., "DDAVP Nasal Spray Treatment for Menorrhagia in Women With Inherited Bleeding Disorders: A Randomized Placebo-Controlled Crossover Study," *Haemophilia* 8: 787-793, Blackwell Publishing Ltd, England (2002).

Kolankaya, A. and Arici, A.,"Myomas and Assisted Reproductive Technologies: When and How to Act?" *Obstetrics and Gynecology Clinics of North America* 33: 145-152, Elsevier Inc., United States (2006).

Kouides, P. and Kreuz, W., "Diagnosis and Management of Inherited Von Willebrand Disease in the Next Decade: A Clinical Perspective," *Thrombosis Research 124 Suppl 1*: Elsevier Ltd., England (2009).

Kriplani, A. et al., "Efficacy, Acceptability and Side Effects of the Levonorgestrel Intrauterine System for Menorrhagia," *International Journal of Gynecology and Obstetrics* 97: 190-194, Elsevier Ireland Ltd., Ireland (2007).

Kriplani, A., et al., "Efficacy and Safety of Ormeloxifene in Management of Menorrhagia: A Pilot Study," *Journal of Obstetrics and Gynaecology Research* 35: 746-752, Japan Society of Obstetrics and Gynecology, Japan (2009).

Miller, C.E., "Unmet Therapeutic Needs for Uterine Myomas," *Journal of Minimally Invasive Gynecology* 16(1): 11-21, Elsevier, United States (2009).

Pelage, J-P., et al., "Midterm Results of Uterine Artery Embolization for Symptomatic Adenomyosis: Initial Experience," *Radiology* 234: 948-953, Radiological Society of North America, United States (2005).

Philipp, C.S. et al., "Evaluation of a Screening Tool for Bleeding Disorders in a US Multisite Cohort of Women With Menorrhagia," *American Journal of Obstetrics and Gynecology* 204: 209e1-209e7, Elsevier Inc., United States (2011).

Ravina, J.H., et al., "Value of Preoperative Embolization of Uterine Fibroma: Report of a Multicenter Series of 31 Cases" *Contraception Fertilité* 23: 45-49, S.A.R.L., France (1995).

Reid, P.C., and Virtanen-Kari, S. "Randomised Comparative Trial of the Levonorgestrel Intrauterine System and Mefenamic Acid For the Treatment of Idiopathic Menorrhagia: A Multiple Analysis Using Total Menstural Fluid Loss, Menstrual Blood Loss and Pictorial Blood Loss Assessment Charts," *BJOG an International Journal of Obstetrics and Gynacology 112*: Publishing, England (2005).

Samuel, N.C. and Clark, T.J. "Future Research into Abnormal Uterine Bleeding," *Best Practice and Research Clinical Obstetrics and Gynaecology* 21(6): 1023-1040, Elsevier Ltd., England (2007).

Sankaran, S. and Manyonda I.T., "Mediacl Management of Fibroids," *Best Practice and Research Clinical Obstetrics and Gynaecology* 22(4): 655-676, Elsevier Ltd., England (2008).

Siskin, G.P. et al., "Uterine Artery Embolization for the Treatment of Adenomyosis: Clinical Response and Evaluation with MRI," *American Journal of Roentgenology* 177: 297-302, American Roentgen Ray Society, United States (2001).

Smith, C.L. and O'Malley, B.W. "Coregulator Function: A Key to Understanding Tissue Specificity of Selective Receptor Modulators," *Endocrine Reviews* 25(1): 45-71, The Endocrine Society, United States (2004).

Smith, S.J., et al., "A Clinical Failure of Uterine Fibroid Embolization Due to Adenomyosis," *Journal of Vascular and Interventional Radiology* 10: 1171-1174, Society of Interventional Radiology, United States (1999).

Somigliana, E. et al., "Fibroids and Female Reproduction: A Critical Analysis of the Evidence," *Human Reproductive Update* 13(5): 465-476, Oxford University Press, England (2007).

Spitz, I., "Progesterone Receptor Antagonists," *Current Opinion in Investigational Drugs* 7(10): 882-890, The Thomson Corporation United States (2006).

Tropeano, G. et al., "Non-Surgical Management of Uterine Fibroids," *Human Reproductive Update* 14(3): 259-274, Oxford University Press, England (2008).

Wallach, E.E. and Vlahos, N.F., "Uterine Myomas: An Overview of Development Clinical Features, and Management" *Obstetrics & Gynecology* 104(2): 393-406, Lipincon Williams & Wilkins, United States (2004).

Zakherah, M.S. et al., "Pictorial Blood Loss Assessment Chart in the Evaluation of Heavy Menstrual Bleeding: Diagnostic Accuracy Compared to Alkaline Hematin," *Gynecologic and Obstetric Investigation* 71: 281-284, Kargar, Switzerland (Jan. 2011).

International Search Report for International Application No. PCT/IB2012/053577, European Patent Office, Netherlands, mailed on Oct. 19, 2012.

* cited by examiner

TREATMENT OF EXCESSIVE MENSTRUAL BLEEDING ASSOCIATED WITH UTERINE FIBROIDS

TECHNICAL FIELD

The present invention relates generally to gynecological diseases and in particular to a methods and compositions for reducing heavy menstruation associated with said gynecological diseases following treatment with vascular occlusion methods or thermal related treatment methods.

BACKGROUND OF THE INVENTION

Many patients suffering from gynecological diseases such as fibroids and/or adenomyosis require intervention in order to improve the diseases' symptoms. Usually, treatment choice is guided by the patient's age and desire to preserve fertility and/or her uterus.

Over the last few years a variety of non invasive treatments has become available to women with symptomatic fibroids and provides alternatives to the surgery. For example, Uterine artery embolization (UAE) which was first described in 1995 (Ravina J H, Bouret J M, Fried D et al. Value of preoperative embolization of uterine fibroma: report of a multicenter series of 31 cases. Contracept Fertil Sex 1995; 23: 45-49, and since then this method has become widely used to treat or treating gynecological diseases such as for example fibroids, or more recently adenomyosis, as a less invasive alternative to hysterectomy.

Besides UAE and transvaginal uterine artery occlusion, thermal related treatment methods have provided additional minimally invasive options such as percutaneous laser treatment, cryoablation, thermal myolysis with laser and magnetic resonance imaging (MRI)-guided focused ultrasound.

Overall, clinical studies of UAE patients with fibroids have reported an improvement in menstrual bleeding scores but a significant proportion of patients bleeding is not normalized following the procedure.

On the other hand, the use of anti-progestational agents before a surgical treatment has also been proposed to shrink uterine leiomoymata (WO2007/103510) or to render the patient amenorrheic.

Thus, there remain significant unmet needs for efficient and better long-term therapies for normalizing menstrual bleeding in a patient suffering from a benign gynecological disease and undergoing a vascular occlusion method or thermal related treatment method.

SUMMARY OF THE INVENTION

The present invention provides a method for normalizing menstrual bleeding on the long-term in a subject suffering from a benign gynecological disease comprising administering, before and/or concomitantly and/or after undergoing a vascular occlusion method or a thermal related treatment method, a dosage of a progesterone receptor modulator, or any metabolite thereof.

Also provided is a progesterone receptor modulator, or any metabolite thereof, for use in normalizing menstrual bleeding on the medium term and/or long-term in a subject suffering from a benign gynecological disease characterized in that said progesterone receptor modulator, or any metabolite thereof, is administered, before and/or concomitantly and/or after undergoing a vascular occlusion method or a thermal related treatment method.

DETAILED DESCRIPTION OF THE INVENTION

The present invention relates to a method for normalizing menstrual bleeding on the medium term and/or the long-term in a subject suffering from a gynecological disease comprising administering, before and/or concomitantly and/or after undergoing a vascular occlusion method or a thermal related treatment method, a dosage of a progesterone receptor modulator, or any metabolite thereof.

In a preferred embodiment the invention relates to a method for normalizing menstrual bleeding on the long-term in a subject suffering from a benign gynaecological disease associated with menorrhagia comprising administering, before and/or concomitantly and/or after undergoing a vascular occlusion method or a thermal related treatment method, a dosage of a progesterone receptor modulator, or any metabolite thereof.

In still a preferred embodiment of the invention the dosage is provided daily.

In a further embodiment, the present invention provides a progesterone receptor modulator, or any metabolite thereof, for use in normalizing menstrual bleeding on the medium term and/or long-term in a subject suffering from a benign gynecological disease characterized in that said progesterone receptor modulator, or any metabolite thereof, is administered, before and/or concomitantly and/or after undergoing a vascular occlusion method or a thermal related treatment method.

"Administering", as it applies in the present invention, refers to contact of a therapeutically effective amount of a progesterone receptor modulator, a SPRM, or an active metabolite thereof, to the subject.

The term "normalization" can be defined as a return to a menstrual bleeding which is considered as of normal or weak strength. If objective measures are used normalization would imply reduction of menstrual blood loss to <80 ml per menstrual cycle.

The term "medium-term" in relation to the expression "normalizing menstrual bleeding" refers to a period of approximately 3 months or longer, and long-term refers to a period of approximately 6 months or longer.

Usually, the "subject" is well-recognized in the art, and, is used herein to refer to a mammal, and, more preferably, a human being, and even more preferably a human female.

The term "comprise" or "comprising" is generally used in the sense of include/including, that is to say permitting the presence of one or more features or components. Additionally, the term "comprising" also encompasses the term "consisting".

As used in the specification and claims, the singular form "a", "an" and "the" include plural references unless the context clearly dictates otherwise.

As used herein, "at least one" means "one or more."

The gynecological disease of the present invention will be selected among the group comprising uterine fibroids and adenomyosis, or a combination of these two diseases.

Uterine fibroids are benign non-cancerous tumors that originate from the smooth muscle layer, the myometrium and the accompanying connective tissue of the uterus. Uterine fibroids are also known as uterine leiomyoma, myoma, fibromyoma, leiofibromyoma, fibroleiomyoma, and fibroma. Fibroids are the most common benign tumors in females with a prevalence of 20-40% in women of reproductive age (Wallach E E, Vlahos N F. Uterine myomas: an overview of development, clinical features, and management. Obstet Gynecol 2004; 104: 393-406).

Most fibroids are asymptomatic but nearly half of women with fibroids have significant and often disabling symptoms including menorrhagia, pelvic pain, dysmenorrhea and pressure effects. In addition, fibroids that distort the uterine cavity can have adverse effects on fertility (American Society for Reproductive Medicine. Myomas and reproductive function. Fertil Steril 2008; 90: 125-130 and Somigliana E, Vercellini P, Daguati R, et al. Fibroids and female reproduction: a critical analysis of the evidence. Hum Reprod Update 2007; 13: 465-76 and Kolankaya A, Arici A. Myomas and assisted reproductive technologies: when and how to act? Obstet Gynecol Clin North Am 2006; 33: 145-52 and Donnez J, Jadoul P. What are the implications of myomas on fertility? A need for a debate? Hum Reprod 2002; 17: 1424-30).

In such women, heavy uterine bleeding is a leading reason for medical consultation, surgery and work days lost (Collins J, Crosignani P G. Endometrial bleeding. Hum Reprod Update 2007; 13: 421-31).

As described supra, Uterine artery embolization (UAE) has become a method of choice for treating gynecological diseases such as for example fibroids as a less invasive alternative to hysterectomy. However, UAE alleviate bleeding symptoms in only a few patients over a long-term period.

Adenomyosis, also known as endometriosis interna, is characterized by the presence of ectopic glandular tissue found in muscle. It usually refers to ectopic endometrial tissue (the inner lining of the uterus) within the myometrium (the thick, muscular layer of the uterus). The condition is typically found in women between the ages of 35 and 50. Patients with adenomyosis can have painful and/or excessive bleeding (menorrhagia). Although minimally invasive therapies have been used to manage adenomyosis, hysterectomy is considered the only procedure that definitely cures the disease. Reports of UAE for adenomyosis have described mainly short-term results (Grow D R, Filer R B. Treatment of adenomyosis with long-term GnRH analogues: a case report. Obstet Gynecol 1991; 78: 538-539) some authors suggesting that UAE resulted in treatment failure (Goodwin S C, McLucas B, Lee M, et al. Uterine artery embolization for the treatment of uterine leiomyomata: midterm results. J Vasc Interv Radiol 1999; 10: 1159-1165; Smith S J, Sewall L E, Handelsman A. A clinical failure of uterine fibroid embolization due to adenomyosis. J Vasc Interv Radiol 1999; 10: 1171-1174). For example, Pelage et al (Pelage J P, Jacob D, Fazel A, et al. Midterm results of uterine artery embolization for symptomatic adenomyosis: initial experience. Radiology 2005; 234: 948-953) reported that only five of nine patients who underwent UAE for pure adenomyosis had complete resolution of abnormal bleeding after 24 months.

Since about 35 to 55% of patients suffering from adenomyosis have coexisting fibroids (Siskin G P, Tublin M E, Stainken B F, Dowling K, Dolen E G. Uterine artery embolization for the treatment of adenomyosis: clinical response and evaluation with MRI. AJR 2001; 177: 297-302), the present invention also considers a method for normalizing menstrual bleeding on the long-term in a subject suffering from a gynecological disease wherein the gynecological disease is uterine fibroids and adenomyosis.

The gynecological diseases of the invention are usually treated by vascular occlusion or by thermal related treatment method.

Non limiting examples of vascular occlusion methods comprise uterine artery embolization (UAE) and uterine artery occlusion. UAE method can for example be transvaginal, abdominal or per laparoscopy.

Uterine Artery Embolization, also called Uterine fibroid embolization (UFE) is a minimally invasive treatment for gynecological disease, in particular for fibroids. In a UFE procedure, physicians use an x-ray camera called a fluoroscope to guide the delivery of small particles to the uterus and fibroids. The small particles are injected through a thin, flexible tube called a catheter. These block the arteries that provide blood flow, causing the fibroids to shrink. Nearly 90% of women with fibroids experience relief of their symptoms. Because the effect of uterine fibroid embolization on fertility is not fully predictable, UFE is typically offered to women who no longer wish to become pregnant.

Transvaginal temporary uterine artery occlusion is an alternative method of reducing blood flow in the uterine arteries for the treatment of uterine fibroids. The procedure is performed by placing a Doppler ultrasound-enabled transvaginal clamp in the vaginal formices and, guided by Doppler ultrasound auditory signals, positioning it to occlude the arteries by mechanical compression against the cervix. The clamp is left in place for 6 hours and then removed. Potential advantages of this technique over UAE are no radiation exposure, no risk of non-target embolization, and the absence of significant post-procedure pain in most patients (Tropeano G, Amoroso S, Scambia G. Non-surgical management of uterine fibroids. Hum. Reprod. Update 2008: 14 (3): 259-274)

As used herein, thermal related treatment method refers to a method selected from the non limiting group comprising thermal myolysis with laser, percutaneous laser treatment, radiofrequency treatment, cryomyolysis, and magnetic resonance-guided focused ultrasound.

In case of fibroids, myolysis involves the use of a laser to directly damage the myoma cells and vessels responsible for the myoma blood supply by coagulative necrosis. This may cause the fibroid to shrink and eventually fibroid cells to necrose. Myolysis is one of the less invasive options for the treatment of uterine fibroids. It is generally recommended for smaller fibroids, but not as helpful for larger ones. The treatment is not usually recommended for patients who hope to have children, because it can cause serious pregnancy complications; these can be dangerous to both mother and child, such as uterine scarring and infection.

During the treatment, a patient is given anesthesia and then a laparoscope is introduced in the peritoneal cavity (or an hysteroscope is inserted in the uterus). Next, a laser or high frequency electric current is administered to the fibroid itself, to directly damage the myoma cells by coagulative necrosis. This acts to cut off the blood supply to the fibroid without doing the same to the surrounding tissue. Once the blood supply to the fibroid is cut off, the fibroid ceases growing, shrinks, and eventually dies.

In the MRI guided percutaneous laser treatment of uterine fibroids, needles are inserted under MR guidance into the centre of the targeted uterine fibroid through an area of skin that has been anaesthetized. Bare laser fibers are inserted down the center of each of the needles into the targeted fibroid. Laser energy is then used to destroy the fibroid. The use of the lasers percutaneously under MR guidance enables the doctor to accurately target the fibroids before applying the thermal energy. MR imaging allows thermal recording of the fibroid in real time throughout the treatment using the heat sensitivity of the MR signal, minimizing damage to the surrounding area.

The radiofrequency ablation method is performed by using an electrical current instead of a laser. It is a minimally invasive technique that uses a needle-like device to heat the fibroid with low frequency electrical current. This technique, called the Halt procedure, begins with the insertion of a laparoscopic camera into the abdomen to visualize the abdomen. An intra-abdominal ultrasound probe is inserted through a second incision to determine the size and location of the fibroids. A third incision, three in total, is used to insert the Halt device. The device burns the cells, which are later reabsorbed by the body. This is an outpatient procedure, but it does require general anesthesia.

Another method of uterine fibroid treatment, called cryomyolysis, utilizes a similar technique, but instead of a laser or electrical current, liquid nitrogen is used to freeze the tissue. This also causes it to stop growing and shrink to a less disruptive size.

MRI-guided focused ultrasound (MRgFUS) is a new minimally invasive method of thermal treatment for treating fibroids that received the FDA approval in 2004. With this technique, high-intensity ultrasound waves pass through the anterior abdominal wall and converge into a precise target point within the fibroid to cause a temperature rise (55-90° C.) sufficient to induce coagulative necrosis within a few seconds. Concurrent MRI allows accurate tissue targeting and real time temperature feedback, thereby achieving controlled localized thermal treatment. The treatment itself consists of consecutive exposures to focused ultrasound energy (sonications) each one lasting ~20 s and resulting in a small (~0.5 cm$^3$) bean shaped ablated volume. Between sonications there is a pause of ~90 s to elapse for the tissue to return to its baseline temperature. Multiple sonications are required to cover the entire target volume, which is typically limited to a maximum of 150 cm$^3$ of tissue and total procedure time is usually over 3 h. Patients are usually discharged home ~1 hour after the end of the procedure and return to usual activities, on average, within 48 h.

Preferably, the progesterone receptor modulator of the invention is a selective progesterone receptor modulator (SPRM), or any metabolite thereof. As used herein "a selective progesterone receptor modulator" or "SPRM" represents a class of progesterone receptor ligands that exerts clinically relevant tissue-selective progesterone agonist, antagonist, or partial (mixed) agonist/antagonist effects on various progesterone target tissues in an in-vivo situation depending on the biological action studied (Smith C L and O'Malley B W, Coregulator function: a key to understanding tissue specificity of selective receptor modulators in Endocr Rev 2004; 25: 45-71.)

Also preferably, the SPRM of the invention is ulipristal (acetate), formerly known as CDB-2914. The chemical formula of ulipritual is 17α-acetoxy-11β-[4-N,N-dimethylaminophenyl)-19-norpregna-4,9-diene-3,20-dione. It is a well-known steroid, more specifically a 19-norprogesterone, which possesses antiprogestational and antiglucocorticoidal activity. This compound, and methods for its preparation, are described in U.S. Pat. Nos. 4,954,490, 5,073,548, and 5,929,262, and international patent applications WO020041065405 and WO2004/078709. Properties of this compound are further described in (Blithe D L, Nieman L K, Blye R P, Stratton P. Passaro M. Development of the selective progesterone receptor modulator CDB-2914 for clinical indications. *Steroids* 2003; 68: 1013-1017).

An "active metabolite", as used herein, refers to a product produced through metabolism in the body of a specified compound, in the present case a PRM or a SPRM, or salt thereof and which exhibits the same biological activity as the specified PRM or SPRM.

Throughout the specification (description and claims) and for the ease of reading, the terms "progesterone receptor modulator", "selective progesterone receptor modulator (SPRM)", and "metabolite thereof", refer also to the salts of said respective progesterone receptor modulator, selective progesterone receptor modulator or metabolite thereof.

Active metabolites of ulipristal, or of a salt thereof, may be identified using routine techniques known in the art and their activities determined using tests such as those described herein. Such metabolites may result for example from the oxidation, reduction, hydrolysis, amidation, deamidation, esterification, deesterification, enzymatic cleavage, and the like, of the administered ulipristal or of a salt thereof. Accordingly, the invention includes active metabolites of ulipristal or of a salt thereof, including compounds produced by a process comprising contacting a compound of this invention with a mammal for a period of time sufficient to yield a metabolic product thereof. Such metabolite may also be produced in vitro by oxidation, reduction, hydrolysis, amidation, deamidation, esterification, deesterification, or enzymatic cleavage of the corresponding ulipristal or salt thereof. Examples of metabolites of ulipristal (CDB-2914), include those described in Attardi B J, Burgenson J. Hild S A, Reel J R. In vitro antiprogestational/antiglucocorticoid activity and progestin and glucocorticoid receptor binding of the putative metabolites and synthetic derivatives of CDB-2914. CDB-4124, and mifepristone. J. Steroid Biochem. Mol. Biol. 2004; 88: 277-288. e.g. monodemethylated CDB-2914 (CDB-3877); didemethylated CDB-2914 (CDB-3963); 17 alpha-hydroxy CDB-2914 (CDB-3236); aromatic A-ring derivative of CDB-2914 (CDB-4183).

The progesterone receptor modulator, the SPRM, or a metabolite thereof, may be administered by any convenient route, including oral, buccal, sublingual, parenteral, transdermal, vaginal, rectal, etc. For a brief review of present methods for drug delivery, see. Langer, Science 1990; 249: 1527-1533, which is incorporated herein by reference. Methods for preparing administrable compounds are known or are apparent to those skilled in the art and are described in more detail in, for example, Remington's Pharmaceutical Science, 17th Ed., Mack Publishing Company, Easton, Pa. (1985), which is incorporated herein by reference, and which is hereinafter referred to as "Remington."

Unit dosages of immediate-release formulations are preferred.

For solid compositions, conventional nontoxic solid carriers may be used which include, for example, pharmaceutical grades of mannitol, lactose, starch, magnesium stearate, sodium saccharine, talcum, cellulose, glucose, sucrose. For oral administration, a pharmaceutically acceptable nontoxic composition is formed by incorporating any of the normally employed excipients, such as those carriers previously listed.

The mode of administration possibilities include tablets, capsules, lozenges, pills, transdermal patches, dental pastes, suppositories, inhalants, solutions, ointments, parenteral depots, vaginal rings, vaginal gels and intra-uterine delivery systems.

Oral solid dosage forms are preferentially compressed tablets or capsules. Compressed tablets may contain diluents to increase the bulk of the progesterone receptor modulator, the SPRM, or a metabolite thereof, so that production of a compressed tablet of practical size is possible. Binders, which are agents which impart cohesive qualities to powdered materials may be also necessary. Povidone, starch, gelatin, sugars such as lactose or dextrose, and natural and synthetic gums may be used. Disintegrants are generally necessary in the tablets to facilitate break-up of the tablet. Disintegrants include starches, clays, celluloses, algins, gums and crosslinked polymers. Lastly small amounts of materials known as lubricants and glidants are included in the tablets to prevent adhesion of the tablet material to surfaces in the manufacturing process and to improve the flow characteristics of the powder material during manufacture. Colloidal silicon dioxide is most commonly used as a glidant and compounds such as talc, magnesium stearate or stearic acids are most commonly used as lubricants. Procedures for the production and manufacture of compressed tablets are well known by those skilled in the art (See Remington).

Capsules are solid dosage forms using preferentially either a hard or soft gelatin shell as a container for the mixture of the progestogen agent or progesterone receptor modulator and inert ingredients. Procedures for production and manufacture of hard gelatin and soft elastic capsules are well known in the art (See Remington).

The oral route is preferred. Other routes of administration can be suitable in comparison with oral routes using blood levels to provide clinical success.

In cases where the progesterone receptor modulator, a SPRM, or a metabolite thereof, is included in a solution, the formulation may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, among others.

Useful intranasal formulations of a progesterone receptor modulator, a SPRM, or a metabolite thereof may contain at least one stabilizer and/or one surfactant. Among the pharmaceutically acceptable surfactants are polyoxyethylene castor oil derivatives, such as polyoxyethylene-glycerol-triricinoleate, also known as polyoxyl 35 caster oil (CREMOPHOR EL), or poloxyl 40 hydrogenated castor oil (CREMOPHOR RH40) both available from BASF Corp.; mono-fatty acid esters of polyoxyethylene (20) sorbitan, such as polyoxyethylene (20) sorbitan monolaurate (TWEEN 80), polyoxyethylene monostearate (TWEEN 60), polyoxyethylene (20) sorbitan monopalmitate (TWEEN 40), or polyoxyethylene 20 sorbitan monolaurate (TWEEN 20) (all available from ICI Surfactants of Wilmington, Del.); polyglyceryl esters, such as polyglyceryl oleate; and polyoxyethylated kernel oil (LABRAFIL, available from Gattefosse Corp.). Preferably, the surfactant will be between about 0.01% and 10% by weight of the pharmaceutical composition. Among the pharmaceutically useful stabilizers are antioxidants such as sodium sulfite, sodium metabisulfite, sodium thiosulfate, sodium formaldehyde sulfoxylate, sulfur dioxide, ascorbic acid, isoascorbic acid, thioglycerol, thioglycolic acid, cysteine hydrochloride, acetyl cysteine, ascorbyl palmitate, hydroquinone, propyl gallate, nordihydroguaiaretic acid, butylated hydroxytoluene, butylated hydroxyanisole, alpha-tocopherol and lecithin. Preferably, the stabilizer will be between about 0.01% and 5% by weight of the pharmaceutical composition. Suspensions may also include chelating agents such as ethylene diamine tetraacetic acid, its derivatives and salts thereof, dihydroxyethyl glycine, citric acid and tartaric acid among others. Additionally, proper fluidity of a suspension can be maintained, for example, by the use of coating materials such as lecithin, by the maintenance of the required particle size in the case of dispersions and by the use of surfactants, such as those previously mentioned. Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or (a) fillers or extenders such as starches, lactose, sucrose, glucose, mannitol and silicic acid; (b) binders such as carboxymethylcellulose, alginates, gelatin, polyvinylpyrrolidone, sucrose and acacia; (c) humectants such as glycerol; (d) disintegrating agents such as agar-agar, calcium carbonate, potato or tapioca starch, alginic acid, certain silicates and sodium carbonate; (e) solution retarding agents such as paraffin; (f) absorption accelerators such as quaternary ammonium compounds; (g) wetting agents such as cetyl alcohol and glycerol monostearate; (h) absorbents such as kaolin and bentonite clay; and (i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Preferably the amount of progesterone receptor modulator, SPRM, or a metabolite thereof is effective to normalize menstrual bleeding on the long-term in a mammal suffering from a gynecological disease and undergoing a vascular occlusion method or a thermal related treatment method, without clinically significant antiglucocorticoid activity.

Preferably, the SPRM, or any metabolite thereof, is selected from the list comprising CDB-2914, mifepristone, asoprisnil, proellex, onapristone, org33628, tanaproget, tanaproget-combo, WAY 166989, NSP 989, NSP-combo, 11[beta]-((4-N,N-Dimethylamino)-phenyl-17[beta]-hydroxy-17[alpha]-propinyl-4,9(10)-estradien-3-one-(RU-38486), 11[beta]-((4-N,N-dimethylamino)-phenyl)-17[beta]-hydroxy-18-methyl-17[alpha]-propinyl-4,9(10)-estradien-3-one, 11[beta]-((4-N,N-dimethylamino)-phenyl)-17[alpha][beta]-hydroxy-17a[alpha]-propinyl-D-homo-4,9(10),16-estratien-3-one, 11[beta]-p-methoxyphenyl-17[beta]-hydroxy-17[alpha]-ethinyl-4,9(10)-estradien-3-one, 11[beta]-(4-acetylphenyl)-17[beta]-hydroxy-17[alpha]-(prop-1-inyl)-4,9(10)-estradien-3-one, 11[beta]-(4-dimethylaminophenyl)-17[alpha]-hydroxy-17[beta]-(3-hydroxypropyl)-13[alpha]-methyl-4,9-gonadien-3-one, (Z)-11[beta]-[4-(dimethylamino)phenyl]-17[beta]-hydroxy-17[alpha]-(3-hydroxy-1-propenyl)-estr-4-en-3-one-5,11[beta], 19-(4-acetylphenyl)-17[beta]-hydroxy-17[alpha]-(3-hydroxyprop-1-(Z)-enyl)-4, 9(10)-estradien-3-one, 11[beta], 19-(4-cyanophenyl)-17[beta]-hydroxy-17[alpha]-(3-hydroxyprop-1-(Z)-enyl)-4-androsten-3-one or 11[beta], 19-(4-(3-pyridinyl)-o-phenylene)-17[beta]-hydroxy-17[alpha]-(3-hydroxyprop-1-(Z)-enyl)-4-androsten-3-one, 17[alpha]-acetoxy-21-methoxy-11β-[4-N,N-dimethylaminophenyl]-19-norpregna-4,9-diene-3,20-dione (CDB 4124).

Most preferably, the selective progesteron receptor modulator is CDB 2914 (Ulipristal), or any metabolite thereof.

According to this invention, the SPRM, and in particular ulipristal or any metabolite thereof, will be administered before and/or concomitantly and/or after undergoing a vascular occlusion method or a thermal related treatment method. This includes the chronic intermittent regimen in case of longer administration prior to intervention.

Ulipristal, or any metabolite thereof, will be administered preferably daily, by oral route for a period of 1 to up to 120 days, most preferably for a period of 84 days (12 weeks). This administration period takes place before, and is finished when the subject is undergoing the vascular occlusion method or the thermal related treatment method.

Alternatively the administration period starts during a period before the subject is undergoing the vascular occlusion method or the thermal related treatment methods and is not finished when said vascular occlusion method or said thermal related treatment method is performed.

Also alternatively, the administration period starts concomitantly and/or after undergoing the vascular occlusion method or the thermal related treatment methods.

The applicants have shown a synergistic effect between i) the administration of a progesterone receptor modulator, a SPRM, or a metabolite thereof, and ii) a vascular occlusion method or a thermal related treatment method, for providing a long-term normalization of the menstrual bleeding that lasts or persists at least 6 months after undergoing said vascular occlusion method or said thermal related treatment method.

As show in Table 2, the number of ulipristal treated patients that had a PBAC score <75 is considerably higher when the patients had UAE compared to the patients that were not treated with UAE (Table 2, 3 months after treatment stop group 2: 15%, group 3: 17% vs group 4: 36% and group 5: 60%). This effect does not result from the mere effects of a treatment with ulipristal alone (group 3: 17%) and a treatment with UAE alone (group 4: 25%).

Normalization of menstrual bleeding can be assessed by evaluating the menstrual blood loss (MBL). The man skilled in the art is familiar with methods to evaluate MBL. This assessment is done by the subject and the treating physician.

MBL evaluation can for example be done by using a diary to assess menstrual blood loss, or a pictorial blood-loss assessment chart (PBAC). In this case, menstrual bleeding is considered normalized when the pictorial blood-loss assessment chart (PBAC) score is equal or less than 100, preferably equal or less than 75.

PBAC is a validated self-reporting tool for assessing menstrual blood loss (Higham J M, O'Brien P M, Shaw R W. Assessment of menstrual blood loss using a pictorial chart. Br. J. Obstet. Gynaecol. 1990; 97: 734-739; Janssen C A. A simple visual assessment technique to discriminate between menorrhagia and normal menstrual blood loss. Eur. J. Obstet. Gynecol. Reprod. Biol. 1996; 70: 21-22; Philipp C S. Faiz A. Heit J A et al. Evaluation of a screening tool for bleeding disorders in a US multisite cohort of women with menorrhagia. American Journal of Obstetrics and Gynecology 2011; 204: 209; Zakherah M S, Sayed G H, El-Nashar S A, Shaaban M M. Pictorial blood loss assessment chart in the evaluation of heavy menstrual bleeding: Diagnostic accuracy compared to alkaline hematin. Gynecol. Obstet. Invest. 2011; 71:281-284). Patients are provided with standardized sanitary materials and record daily on a chart, the number of tampons and towels used with the degree to which individual items were soiled with blood (see Appendix for visualisation of a PBAC chart). A slightly stained tampon/towel scores 1. A completely saturated tampon with blood scores 10 and a completely saturated towel with blood scores 20. PBAC has been correlated with menstrual blood loss assessed by a standard chemical method i.e. alkaline haematin (r=0.847). Menorraghia is defined as a PBAC >100 which correspond to a blood loss of >80 mL. A PBAC of 400 corresponds to a blood loss of around 300 mL or approximately 80 tampons/towels used.

PBAC has been widely used for evaluating drugs or devices for the treatment of heavy menstrual bleeding such as desmopressin (Kadir R A, Lee C A, Sabin C A. Pollard D, Economides DL. DDAVP nasal spray for treatment of menorrhagia in women with inherited bleeding disorders: A randomized placebo-controlled crossover study. Haemophilia 2002; 8: 787-793), tranexamic acid (Kouides P, Kreuz W. Diagnosis and management of inherited von Willebrand disease in the next decade: a clinical perspective. Thromb. Res. 2009; 124: 1), ormeloxifene (Kriplani A, Kulshrestha V, Agarwal N. Efficacy and safety of ormeloxifene in management of menorrhagia: A pilot study, Journal of Obstetrics and Gynaecology Research 2009; 35: 746-752), levonorgestrel IUD (Reid P C, Virtanen-Kari S. Randomised comparative trial of the levonorgestrel intrauterine system and mefenamic acid for the treatment of idiopathic menorrhagia: A multiple analysis using total menstrual fluid loss, menstrual blood loss and pictorial blood loss assessment charts. BJOG Int. J. Obstet. Gynaecol. 2005; 112: 1121-1125; Kriplani A. Singh B M. Lal S, Agarwal N. Efficacy, acceptability and side effects of the levonorgestrel intrauterine system for menorrhagia. Int. J. Gynecol. Obstet. 2007; 97: 190-194), and device for endometrial ablation (Busfield R A, Farquhar C M, Sowter M C et al. A randomized trial comparing the levonorgestrel intrauterine system and thermal balloon ablation for heavy menstrual bleeding. Obstet. Gynecol. Surv. 2006; 61: 444-445).

The "hematite method" is another possible method of MBL evaluation. It consists in analyzing the amount of hemoglobin lost during the menstruation, collected in sanitary towels.

Surprisingly enough, the Applicants have shown that long-term normalization of the menstrual bleeding after undergoing said vascular occlusion method or said thermal related treatment methods is more important with therapeutically effective dose or amount of 5 to 20 mg of ulipristal, more important with a dose of 7 to 20 mg.

Particularly preferred dosages are 7 mg, 8 mg, 9 mg, 10 mg, 11 mg, 12 mg, 13 mg, 14 mg, 15 mg, 16 mg, 17 mg, 18 mg, 19 mg and 20 mg.

The Applicants have shown that long-term normalization of the menstrual bleeding after undergoing said vascular occlusion method or said thermal related treatment methods is more important with therapeutically effective daily dose or daily amount of 7 to 20 mg of ulipristal, more important with a dose of 7 mg and even more important with a dose of about 10 mg, compared to 5 mg.

A dose selected from the list of 7 mg, 8 mg, 9 mg, 10 mg, 11 mg, 12 mg, 13 mg, 14 mg, 15 mg, 16 mg, 17 mg, 18 mg, 19 mg or 20 mg per day is thus most preferred.

This invention also envisages the use of an SPRM e.g. ulipristal, or a metabolite thereof, in a pharmaceutically acceptable salt form. Examples of such salts may include sodium, potassium, calcium, aluminum, gold and silver salts. Also contemplated are salts formed with pharmaceutically acceptable amines such as ammonia, alkyl amines, hydroxyalkylamines. N-methylglucamine and the like. Certain basic compounds also form pharmaceutically acceptable salts, e.g., acid addition salts. For example, pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, pamoic, methanesulfonic and other mineral and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

Alternatively, or additionally, it will become apparent that ulipristal, or a metabolite thereof, may be administered alone or in combination with other treatments, therapeutics or agents, either simultaneously or sequentially dependent upon the condition to be treated. For example, ulipristal, or a metabolite thereof, in the method of the invention may be administered in association with a pain killer or iron and/or sequentially with a GnRH agonist or antagonist or a progesteron.

The present invention also contemplates a kit for normalizing menstrual bleeding on the long-term in a subject suffering from a benign gynecological disease comprising the progesterone receptor modulator, or any metabolite thereof, optionally with reagents and/or instructions for use.

Generally, the Kit comprises a container and a label or package insert on or associated with the container. Suitable containers include, for example, bottles, vials, syringes, etc. The containers may be formed from a variety of materials such as glass or plastic. The container holds the progesterone receptor modulator, or any metabolite thereof of the invention which is effective for normalizing menstrual bleeding on the long-term in a subject suffering from a benign gynecological disease. The label or package insert indicates that the composition is used for treating the condition of the invention.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended Claims, and all changes which come within the meaning and range of equivalency are intended to be embraced therein.

Various references are cited throughout this specification, each of which is incorporated herein by reference in its entirety.

The foregoing description will be more fully understood with reference to the following Examples. Such Examples, are, however, exemplary of methods of practicing the present invention and are not intended to limit the scope of the invention.

EXAMPLES

Example 1

Effect of 5 mg and 10 mg Oral Ulipristal Acetate Therapy Prior Uterine Artery Embolization on Uterine Fibroids 1. Clinical Study A double-blind, randomized, placebo-controlled study was conducted to evaluate the long term effect of ulipristal acetate in the treatment of uterine fibroids. Patients included premenopausal women 18-50 years with heavy uterine bleeding due to uterine fibroids who were eligible for surgery. These patients met the criteria of a Pictorial Bleeding Assessment Chart (PBAC) score >100 during days 1-8 of menstruation.

The patients were randomized in a 2:2:1 manner to receive for 12 weeks, either ulipristal acetate (UPA) 5 mg or ulipristal acetate 10 mg or placebo. In addition, all patients received concomitant iron therapy (1 tablet of 80 mg or iron once daily, Tardyfero®). The reference to 2:2:1 means that for every 5 patients, two would be randomized to receive UA 5 mg, two to receive UA 10 mg and one to receive placebo.

Forty-eight patients received a daily placebo treatment, 95 patients received a daily dose of 5 mg ulipristal acetate (Esmya®), and 98 patients received a daily dose of 10 mg ulipristal acetate (Esmya®). Of these patients, 115 patients did not undergo surgery: 26 patients in the placebo group (group 1), 48 subjects in the 5 mg group (group 2) and 41 subjects in the 10 mg group (group 3). Thirty-three subjects underwent a Uterine Artery Embolization at or after week 13: 4 patients in the placebo group (group 4), 11 patients in the 5 mg ulipristal (Esmya®) group (group 5) and 18 patients in the 10 mg ulipristal (Esmya®)) group (group 6).

2. Parameters Assessed

For study enrollment as well as follow-up assessment, menstrual bleeding was assessed using the pictorial blood loss assessment chart (PBAC) developed by Higham and colleagues (Higham J M, O'Brien P M, Shaw R W. Assessment of menstrual blood loss using a pictorial chart. Br J Obstet Gynaecol 1990; 97:734-9). The PBAC is one of the current standard methods used to objectively estimate menstrual blood loss and diagnose menorrhagia. Abnormal bleeding is defined as PBAC score >100 over 8 days of menstruation. Normal menstrual bleeding PBAC is <75. Amenorrhea is PBAC=0.

The PBAC score was assessed before treatment (Baseline), at week 13 after the end of treatment with ulipristal, at 3 months and 6 months after Uterine Artery Embolization.

The PBAC and the % of patients with a PBAC <75 was reported before treatment (Baseline), at week 13 after the end of treatment with ulipristal, at 3 months and 6 months after the treatment stop.

3. Results

The results are shown in Tables 1 and 2.

TABLE 1

|  | No UAE or any other surgery | | | with UAE performed after treatment stop (13 weeks onwards) | | |
| --- | --- | --- | --- | --- | --- | --- |
|  | Placebo Group 1 | Esmya 5 mg Group 2 | Esmya 10 mg Group 3 | Placebo Group 4 | Esmya 5 mg Group 5 | Esmya 10 mg Group 6 |
| n | 26 | 50 | 41 | 4 | 11 | 16 |
| PBAC at baseline* | 470 +/− 328 | 419 +/− 281 | 340 +/− 187 | 722 +/− 347 | 490 +/− 231 | 375 +/− 135 |
| PBAC at week 13 of treatment* | 392 +/− 305 | 13 +/− 69 | 2 +/− 13 | 414 +/− 296 | 25 +/− 60 | 0 +/− 0 |
| PBAC 3 months after treatment stop* | 421 +/− 321 | 337 +/− 300 | 417 +/− 669 | 241 +/− 96 | 202 +/− 102 | 120 +/− 55 |

TABLE 1-continued

|  | No UAE or any other surgery ||| with UAE performed after treatment stop (13 weeks onwards) |||
| --- | --- | --- | --- | --- | --- | --- |
|  | Placebo Group 1 | Esmya 5 mg Group 2 | Esmya 10 mg Group 3 | Placebo Group 4 | Esmya 5 mg Group 5 | Esmya 10 mg Group 6 |
| PBAC 6 months after treatment stop* | 347 +/− 242 | 338 +/− 233 | 203 +/− 161 | 243 +/− 181 | 207 +/− 117 | 136 +/− 70 |

*Mean +/− SD

TABLE 2

|  | No UAE or any other surgery ||| with UAE |||
| --- | --- | --- | --- | --- | --- | --- |
|  | Placebo Group 1 | Esmya 5 mg Group 2 | Esmya 10 mg Group 3 | Placebo Group 4 | Esmya 5 mg Group 5 | Esmya 10 mg Group 6 |
| n | 25 | 46 | 38 | 4 | 11 | 16 |
| % Patient with PBAC < 75 at baseline | 0% | 0% | 0% | 0% | 0% | 0% |
| % Patient with PBAC < 75 at week 13 of treatment | 17% | 98% | 97% | 50% | 100% | 100% |
| % Patient with PBAC < 75, 3 months after end of treatment | 9% | 15% | 17% | 25% | 36% | 60% |
| % Patient with PBAC < 75, 6 months after after end of treatment | 18% | 17% | 26% | 25% | 27% | 53% |

3.1 All patients had a PBAC score >100 at baseline (Table 1, group 1 to 6) and had severe bleeding and associated anemia. None of them had normal menstrual bleeding (Table 2, group 1 to 6).

3.2 At week 13, nearly all ulipristal treated patients had a PBAC score <75 compared to the placebo patients and had controlled (no, weak or normal bleeding) menstrual bleeding (Table 2, group 2: 98%, group 3: 97%, group 5: 100% and group 6: 100% vs placebo group 1: 17% and placebo group 4: 50%).

3.3 At 3 months after the end of treatment with ulipristal acetate or placebo, in the subgroup of patients who did not have UAE, the number of ulipristal treated patients that had a PBAC score <75 is slightly higher compared to the placebo treated patients (Table 2, group 2: 15%, group 3: 17% vs placebo group 1: 9%).

Interestingly, the number of ulipristal treated patients that had a PBAC score <75 is considerably higher when the patients had UAE compared to the patients that were not treated with UAE (Table 2, 3 months after treatment stop group 2: 15%, group 3: 17% vs group 4: 36% and group 5: 60%).

Therefore, these results demonstrate a synergistic effect for controlling menstrual bleeding resulting from the oral administration of ulipristal prior to UAE. This effect does not result from the mere effects of a treatment with ulipristal alone (group 3: 17%) and a treatment with UAE alone (group 4: 25%).

Interestingly, the number of ulipristal treated patients that had a PBAC score <75 is considerably higher when the patients received a 10 mg dose of ulipristal prior UAE compared to the placebo treated patients.

3.5 There is a dose dependence effect that is observed when ulipristal is administered prior UAE at a dose of 10 mg in comparison to 5 mg This dose dependence effect is observed at 3 months after UAE (group 6: 60% vs group 5: 36%) and at 6 months after UAE (group 6: 53% vs group 5: 27%) showing the long term effect of this method for controlling excessive menstrual bleeding in a patient population with uterine fibroids.

The invention claimed is:
1. A method for normalizing excessive menstrual bleeding in a human subject comprising administering to the subject in need thereof, a therapeutically effective dose of a progesterone receptor modulator selected from the group consisting of CDB 2914, mifepristone, asoprisnil, onapristone, org33628, tanaproget, and tanaproget-combo, or a metabolite of CDB 2914 selected from the group consisting of CDB-3877, CDB-3963, CDB-3236, and CDB-4183,
   wherein the subject is suffering from a benign gynecological disease selected from the group consisting of uterine fibroids, adenomyosis, or a combination thereof, and
   wherein the subject is treated with a vascular occlusion method or a thermal related treatment.

2. The method according to claim 1, wherein the vascular occlusion method is selected from the group consisting of uterine artery embolization (UAE) and transvaginal uterine artery embolization.

3. The method according to claim 1, wherein the thermal related treatment method is selected from the group consisting of thermal myolysis with laser, percutaneous laser treatment, radiofrequency ablation, cryomyolysis, and magnetic resonance-guided focused ultrasound.

4. The method according to claim 1, wherein the menstrual blood loss is reduced to <80 ml per menstrual cycle.

5. The method according to claim 1, wherein the menstrual bleeding in the subject is normalized for a period of approximately 6 months or longer.

6. The method according to claim 1, wherein the SPRM is CDB 2914 (Ulipristal), or any metabolite thereof.

7. The method according to claim 6, wherein the CDB 2914 (Ulipristal) or any metabolite thereof is administered at a dose from 5 to 20 mg.

8. The method according to claim 7, wherein the CDB 2914 (Ulipristal), or any metabolite thereof is administered at a dose selected from the group consisting of about 5 mg, about 6 mg, about 7 mg, about 8 mg, about 9 mg, about 10 mg, about 11 mg, about 12 mg, about 13 mg, about 14 mg, about 15 mg, about 16 mg, about 17, about 18 mg, about 19 mg, and about 20 mg.

9. The method according to claim 8, wherein the CDB 2914 (Ulipristal), or any metabolite thereof, is administered at a dose of about 5 mg.

10. The method according to claim 8, wherein the CDB 2914 (Ulipristal), or any metabolite thereof, is administered at a dose of about 7 mg.

11. The method according to claim 8, wherein the CDB 2914 (Ulipristal), or any metabolite thereof is administered at a dose of about 10 mg.

12. The method according to claim 1, wherein the subject is a female.

13. The method according to claim 1, wherein the therapeutically effective dose of the progesterone receptor modulator, or the metabolite, is administered daily.

14. The method according to claim 1, wherein the menstrual bleeding in the subject is normalized for a period of approximately 3 months or longer.

15. The method according to claim 1, wherein the therapeutically effective dose of the progesterone receptor modulator, or the metabolite, is administered to the subject concomitantly, before, or after the subject is treated with the vascular occlusion method or the thermal related treatment method.

16. The method of claim 1, wherein the progesterone receptor modulator is CDB 2914, and wherein the CDB 2914 is administered orally at a dose of about 10 mg to the subject before the subject is treated with the vascular occlusion method or the thermal related treatment method.

17. The method of claim 16, wherein the vascular occlusion method is uterine artery embolization.

18. The method of claim 17, wherein the menstrual bleeding in the subject is normalized for a period of approximately 3 months or longer after the treatment.

19. The method of claim 13, wherein the progesterone receptor modulator or the metabolite of CDB 2914 is administered orally to the human subject.

20. The method of claim 15, wherein the therapeutically effective dose of the progesterone receptor modulator, or the metabolite, is administered to the subject after the subject is treated with the vascular occlusion method or the thermal related treatment method.

* * * * *